(12) United States Patent
Kleinschmidt

(10) Patent No.: US 7,850,765 B2
(45) Date of Patent: Dec. 14, 2010

(54) DISPOSABLE ABSORBER WITH ADAPTER AND LIP SEAL

(75) Inventor: Lothar Kleinschmidt, Krummesse (DE)

(73) Assignee: Dräger Medical GmbH, Lübeck (DE)

( * ) Notice: Subject to any disclaimer, the term of this patent is extended or adjusted under 35 U.S.C. 154(b) by 301 days.

(21) Appl. No.: 12/188,394

(22) Filed: Aug. 8, 2008

(65) Prior Publication Data

US 2009/0107505 A1    Apr. 30, 2009

(30) Foreign Application Priority Data

Oct. 24, 2007   (DE) .................... 10 2007 050 853

(51) Int. Cl.
*A61M 16/22* (2006.01)
*B01D 53/02* (2006.01)

(52) U.S. Cl. .................... 96/147; 55/502; 277/918; 128/205.28

(58) Field of Classification Search ............ 96/118, 96/147, 151; 95/91, 139; 128/205.12, 205.28, 128/205.24; 55/502; 210/450; 277/615, 277/918

See application file for complete search history.

(56) References Cited

U.S. PATENT DOCUMENTS

| | | | | | |
|---|---|---|---|---|---|
| 3,690,283 | A | * | 9/1972 | Pool | 114/67 A |
| 4,664,421 | A | * | 5/1987 | Jones | 277/615 |
| 4,816,047 | A | * | 3/1989 | Neal | 96/137 |
| 5,205,568 | A | * | 4/1993 | Stoll et al. | 277/615 |
| 5,487,380 | A | * | 1/1996 | Grabenkort | 128/204.15 |
| 5,622,544 | A | * | 4/1997 | Shamine et al. | 96/134 |
| 5,755,844 | A | * | 5/1998 | Arai et al. | 55/502 |
| 5,779,772 | A | * | 7/1998 | Unger et al. | 96/137 |
| 5,792,245 | A | * | 8/1998 | Unger et al. | 96/137 |
| 7,097,696 | B2 | * | 8/2006 | Salzman et al. | 96/121 |
| 7,520,922 | B2 | * | 4/2009 | Hoffman et al. | 96/143 |
| 2008/0289505 | A1 | * | 11/2008 | Milomo | 96/134 |

FOREIGN PATENT DOCUMENTS

DE       197 29 739 A1     1/1999

* cited by examiner

*Primary Examiner*—Frank M Lawrence
(74) *Attorney, Agent, or Firm*—McGlew and Tuttle, P.C.

(57) ABSTRACT

An adapter is provided for adapting an absorber container (4) to a breathing system. A seal (405) is employed that has sealing surfaces (55, 56, 57), which extend in a jacket area (34) of a valve crater (15), which limits an outer gas channel. The seal (405) is provided between the absorber container (4) and the adapter.

13 Claims, 10 Drawing Sheets

DISPOSABLE ABSORBER WITH ADAPTER AND LIP SEAL

CROSS REFERENCE TO RELATED APPLICATIONS

This application claims the benefit of priority under 35 U.S.C. §119 of German Patent Application DE 10 2007 050 853.2 filed Oct. 24, 2007, the entire contents of which are incorporated herein by reference.

FIELD OF THE INVENTION

The present invention pertains to an adapter for adapting an absorber container to a breathing system, with a first gas channel 12 and with a second gas channel 14, which extend into the connection area between the absorber container 4 and the adapter.

BACKGROUND OF THE INVENTION

Absorber containers filled with breathing lime are used in anesthesia devices or even diving equipment to bind the $CO_2$ (carbon dioxide) contained in the expired air. Disposable absorbers are frequently used. Further advantages arise from the use of a disposable absorber for the user: direct contact with the breathing lime is avoided during the handling of the absorber container, and there is no exposure to dust. The utilization of the absorber filling is also improved and cost savings are thus achieved, since it is possible to replace the absorber at any time, for example, also during an operation, so that an absorber can be used until the filling is used up completely. As an alternative, refillable absorber containers are used as well. Refilling is then preferably carried out via the bottom, the cover or laterally via the jacket surface of an absorber container.

The absorber container must be able to be replaced simply and rapidly, without respiration being compromised. An absorber of the type mentioned in the introduction appears, for example, from DE 197 29 739 A1.

An absorber container is usually arranged on the existing absorber mount of a breathing system by means of an adapter and optionally an intermediate plate. The interface at the absorber mount of the breathing system or the interface at the intermediate plate forms, together with the interface at the adapter, for example, a bayonet catch. After the two interfaces are fitted into each other and the interfaces are subsequently twisted in relation to one another, the breathing system and the adapter are braced with one another in a gas-tight manner. The absorber container is preferably connected to the adapter via a pivotable mounting plate with integrated spring-loaded latch. The mounting plate has, for example, guide grooves for this for receiving corresponding guide webs of the absorber container. If the mounting plate can be pivoted into an oblique position of approximately 30° in relation to the horizontal, the absorber container will slide by itself into its end position, which is defined by a milled recess in the mounting plate. The spring-loaded latch closes by pivoting the absorber container with the mounting plate against the adapter. A gas-tight connection between the adapter and the absorber container is of particular importance here.

Flat packings, which are buttoned into the adapter and are fastened by undercuts on a cylindrical inner bushing of the adapter, are known in this connection. The flat packings seal flush, flatly and on the front side against cylindrical pipe sockets of the absorber container, and they are also called sealing craters. Unevennesses, contamination due to lime dust or damage to the front surfaces of the sealing craters may lead to leaks.

Inner flat packings are also located on a spring-loaded valve body, which establishes the gas connection between the absorber container and the breathing system during the locking operation. For example, the absorber container is unlocked by pressing a specially marked point of the mounting plate with a finger, and the gas connection between the breathing system and the absorber container is interrupted. At the same time, a bypass is established within the adapter via the spring-loaded valve body, and the gas connection to the environment is interrupted. Respiration takes place in this position without the absorber being switched on.

Another difficulty lies in the fact that strong forces are needed to lock the adapter and the absorber container, because tolerances in the dimensions of the individual components must be absorbed by corresponding deformations of the flat packings. This leads to increased wear and, as a consequence of this, to premature failure of the flat packings.

SUMMARY OF THE INVENTION

A basic object of the present invention is to improve an absorber container and an adapter of the type such that the connection system between the breathing system and the absorber container makes possible a gas-tight connection in a simple manner. A basic object of the present invention is especially to perfect an adapter as well as an absorber container with adapter such that leaks at the seals of the connection system will be avoided.

The adapter according to the present invention for adapting an absorber container to a breathing system comprises:

a first gas channel and a second gas channel, which extend in the connection area between the absorber container and the adapter;

a valve means in the line of the gas channels, which has a seal, which either seals the gas channels against the valve means such that the absorber container is cut off from the line of the gas channels, or seals the gas channels against the valve means such that the absorber container is located in the line between the first gas channel and the second gas channel, and is characterized in that the sealing comprises sealing surfaces, which extend at an angle to the front surface of the absorber container.

In the context of the invention, "at an angle to the front surface of the absorber container" means in connection with the present invention at an angle greater than 10°, preferably greater than 30° and especially preferably greater than 45° relative to the front surface of the absorber container.

The advantage of the adapter according to the present invention is essentially its sealing properties, which are improved by the fact that, for example, not only is an inner and/or outer valve crater of the absorber container in contact with a seal on the front side, but another partial surface, e.g., a jacket surface of the valve crater, at right angles to the front surface of the absorber container, and/or a recessed surface, which is formed as an extension of the valve crater, are designed as sealing surfaces. The sealing surface thus comprises a plurality of partial surfaces sloped or offset in relation to one another, which leads to improved sealing properties.

The partial surfaces may also be divided such that a first partial surface is the front side of a valve crater and another partial surface lies on the jacket surface of the valve crater. Providing a plurality of partial surfaces on the jacket surface, which are assigned to individual sealing lips, is also within the scope of the present invention and is especially preferred.

In a preferred embodiment, the first gas channel is designed as an inner gas channel and the second gas channel as an outer gas channel arranged concentrically thereto.

In addition, it is also advantageous if the sealing surface comprises a sealing crater extending on the front surface to the absorber container and a sealing lip that is in contact with the jacket surface of the sealing crater.

The sealing crater on the absorber container is especially a valve crater of the valve means. A ring-shaped inner valve crater has, for example, a mean diameter of 22 mm (millimeters) in this case, and the internal diameter and the external diameter equal 20 mm and 24 mm, respectively. A ring-shaped outer valve crater has, for example, a mean diameter of 42 mm, and the internal diameter and the external diameter are 40 mm and 44 mm, respectively. The height of the crater, measured from the top side of the absorber container, preferably equals 5.5 mm. The recessed surface joins in a ring-shaped manner from the outside and is located preferably 2.5 mm below the top side of the absorber container, so that the height of the crater in relation to the recessed surface is 8 mm. The recessed surface has an internal diameter of 44 mm and an external diameter of 60.5 mm, and the outer jacket surface of the recessed surface is preferably sloped by 60° in relation to the front surface of the absorber container in the area of the external diameter.

The sealing lips may be in contact with a jacket surface of the sealing crater and/or with a surface recessed on the front side and/or with the front surface of a sealing crater.

In principle, various seals may be combined in one adapter or one absorber container. For example, a plurality of sealing lips may be in contact with an outer sealing crater, and an inner sealing crater may be part of a conventional flat packing and designed as a sealing surface on the front side.

It may be possible to do without seals with sealing lips made of elastomers if, for example, a spring-loaded valve body and a valve crater with suitable surface properties meet bluntly and the pressure conditions on the two sides of the seal do not stress this seal strongly.

In addition, it is especially advantageous if the sealing crater is designed with a ring-shaped form with rounded edges and if more than one sealing lip is in contact with the jacket surface of a sealing crater. In particular, a recessed surface is extended on the front side towards the absorber container in order to arrange a plurality of sealing lips thereon.

The object of the present invention is also accomplished by an absorber container for adaptation to a breathing system, which comprises an adapter according to one of the above-described embodiments.

An exemplary embodiment of the present invention will be explained below on the basis of the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
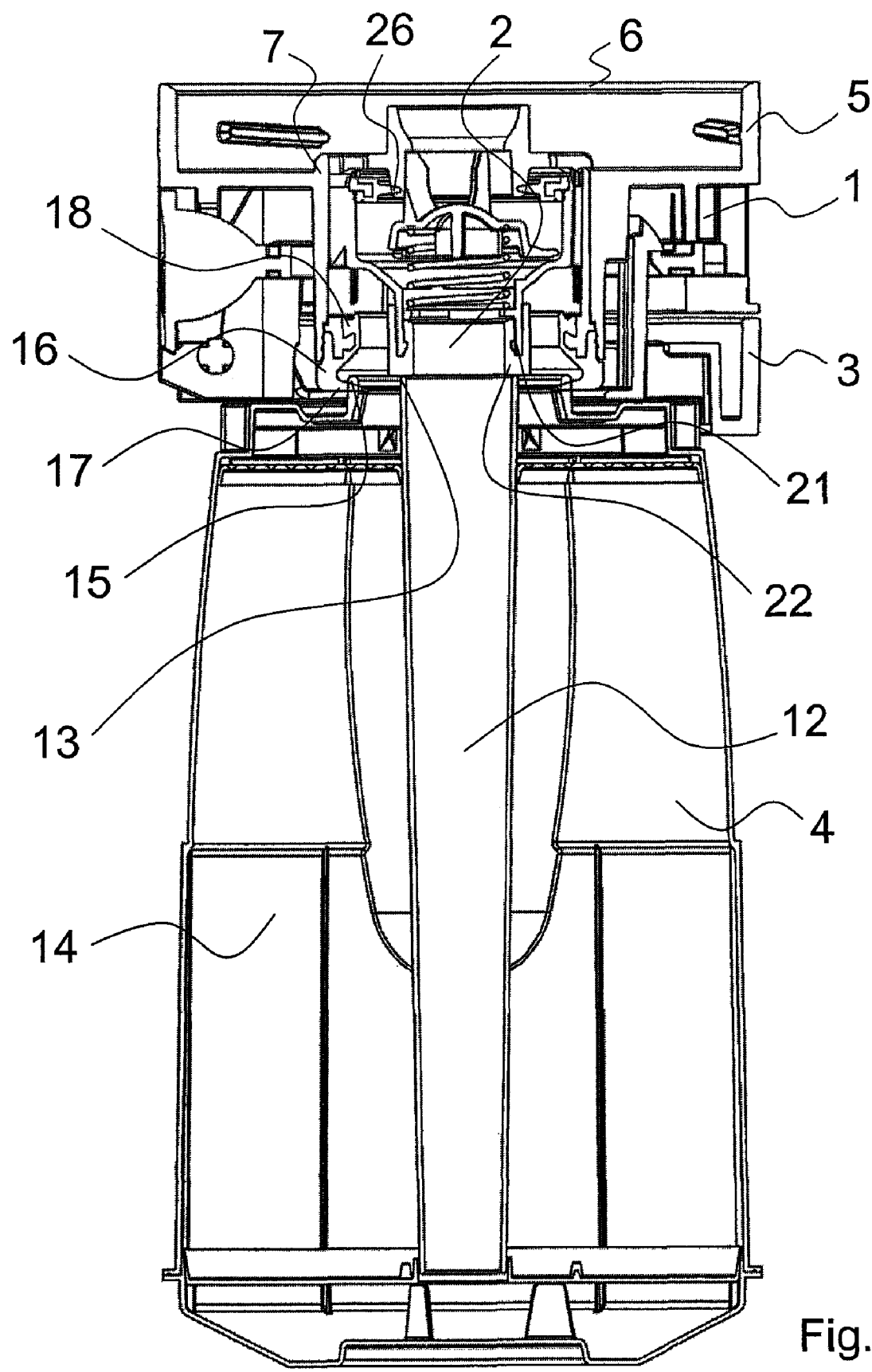
FIG. 1 is a schematic view of a longitudinal section of an absorber container with a connected adapter in the locked position.

Referring to the drawings in particular, FIG. 1 shows a schematic view of a longitudinal section of an absorber container 4 with a connected adapter 1 in the locked position. Adapter 1 has a housing 5 with a connecting branch 6 for connection to a breathing system, not shown more specifically in FIG. 1. To connect the absorber container 4 to the adapter 1, the absorber container 4 is pushed into a mount 3 and pivoted in the direction of the adapter 1, which has already taken place in FIG. 1. The absorber container 4 has an inner gas channel 12 with an inner valve crater (valve seat) 13 and an outer gas channel 14 arranged concentrically thereto with an outer valve crater (valve seat) 15. The inner gas channel 12 describes the path of flow from the breathing system to the absorber container 4 with the connected adapter 1 in the locked position, and the outer gas channel 14 describes the path of flow from the absorber container 4 back to the breathing system with the connected adapter 1 in the locked position.

The inner gas channel 12 extends within the adapter 1 through the interior space of a valve means 2. A first sealing ring 16, which has an outer sealing lip 17 directed towards the absorber container 4 and an inner sealing lip 18, is located on the underside of a guide sleeve 7 for receiving the valve means 2. A wall section 21 of the housing of the valve means 2 is provided at its free end, which extends in the direction of the absorber container 4, with a second sealing ring 22.

When the absorber container 4 is connected to the adapter 1, the outer sealing lip 17 of the first sealing ring 16 is in contact with the outer valve crater 15, and the second sealing ring 22 is in contact with the inner valve crater 13.

Figure 2:
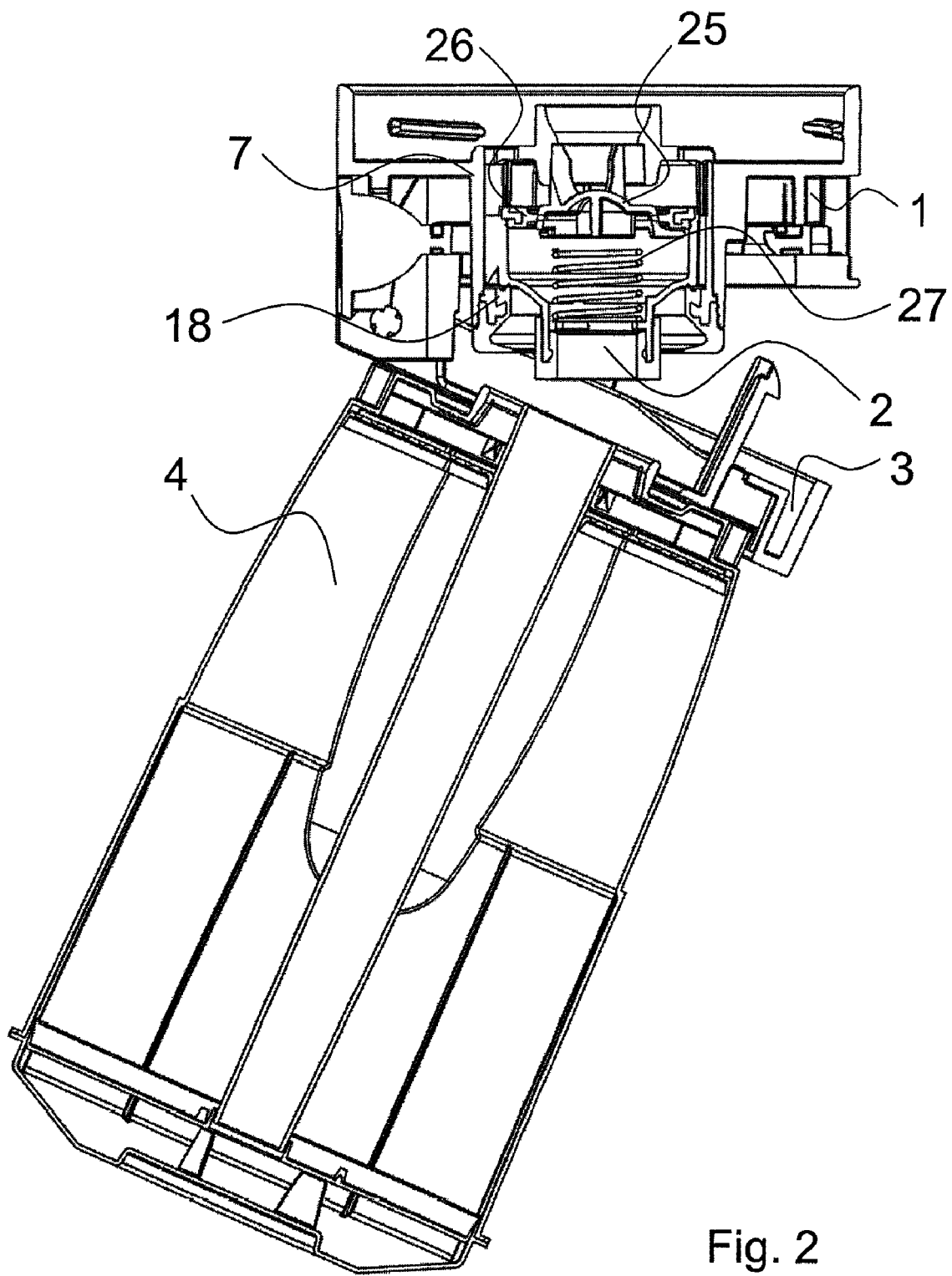
FIG. 2 is a schematic view of a longitudinal section of the absorber container with adapter from FIG. 1 in the pivoted-off position.

FIG. 2 shows a schematic view of a longitudinal section of the absorber container 4 with adapter 1 from FIG. 1 in the pivoted-down position. Identical reference numbers will be used below for the same components as in FIG. 1.

The path of flow extends within the adapter 1 through the interior space of the valve means 2. The inner sealing lip 18 of the first sealing ring 16 is in contact from the outside with the housing of the valve means 2. The inner sealing lip 18 and the housing of the valve means 2 form a sealing area to interrupt the flow of gas from the absorber container 4 when the absorber container 4 is not connected to the adapter 1. A sealing lip 26 is in contact with a valve body 25 on the top side of the valve means 2. The sealing lip 26 and valve body 25, which is pressed against the sealing lip 26 via a compression spring 27, form another sealing area in order to interrupt the flow of gas to the absorber container 4. In the position of the absorber container 4 shown in FIG. 2, the path of flow extends through free spaces within the adapter 1 to the outer gas channel 14 via the inner gas channel 12, without taking the path via the absorber container 4.

Figure 3:
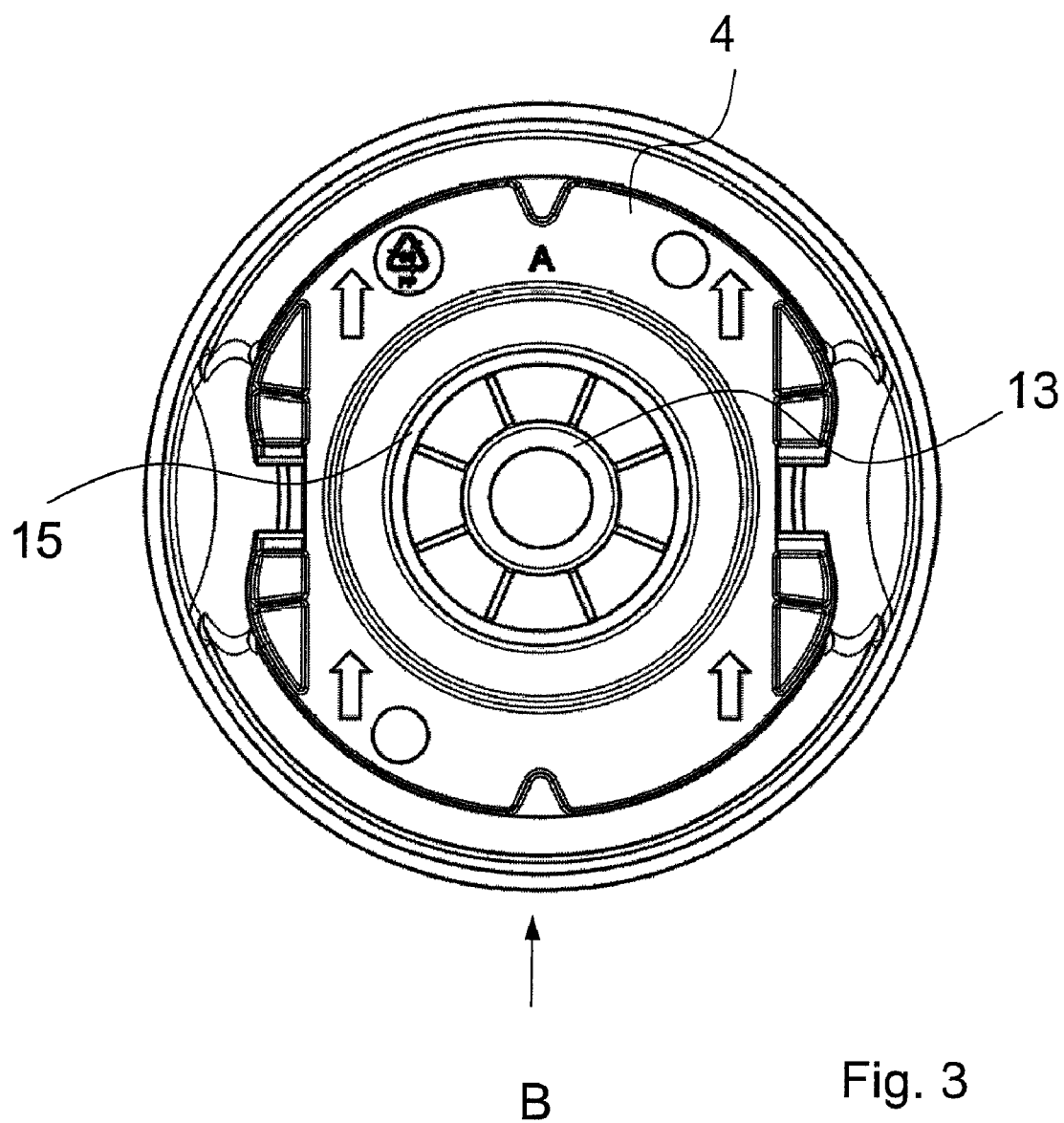
FIG. 3 is a schematic view into the absorber container from FIG. 1 with inner and outer valve craters.

FIG. 3 shows a schematic view into the absorber container 4 with the inner valve crater 13 and the outer valve crater 15.

Figure 4:
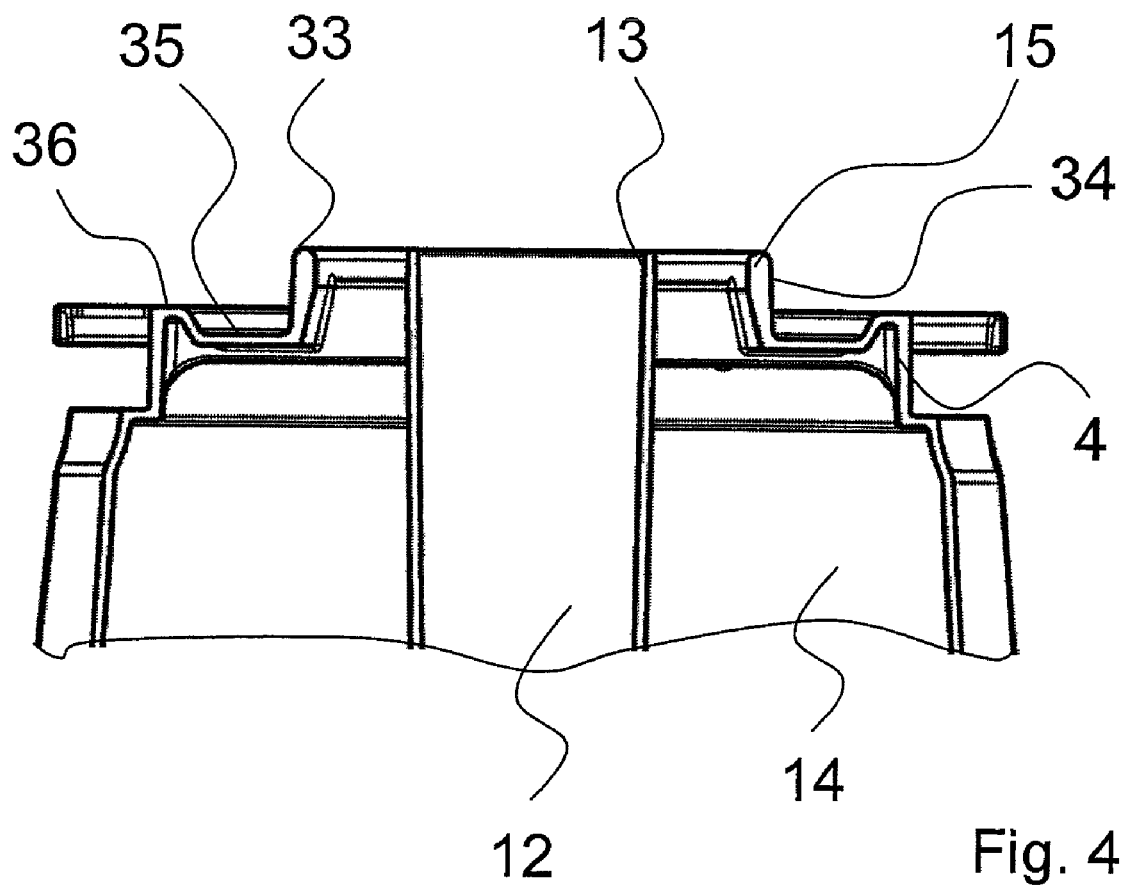
FIG. 4 is a schematic partial view of a cross section of the absorber container from FIG. 1 when viewed in direction B from FIG. 3.

FIG. 4 shows a schematic partial view of a cross section of the absorber container 4 in the direction of view B from FIG. 3 with an inner valve crater 13 and an outer valve crater 15. The outer valve crater 15 has a front surface 33 and a jacket surface 34, which is joined outwardly in an annular pattern by a recessed surface 35 on the top side 36 of the absorber container 4. The outer jacket surface of the recessed surface 35 is sloped by 60° in relation to the top side 36 of the absorber container in the area of the external diameter.

FIGS. 5 through 9 are views of different sealing rings 401, 402, 403, 404, 405 with sealing lips 50, 51, 52, 53, 54 in profile. The sealing rings 401, 402, 403, 404, 405 are the first sealing ring 16. Sealing lips 50, 51, 52, 53, 54 are the outer sealing lip 17.

Figure 5:
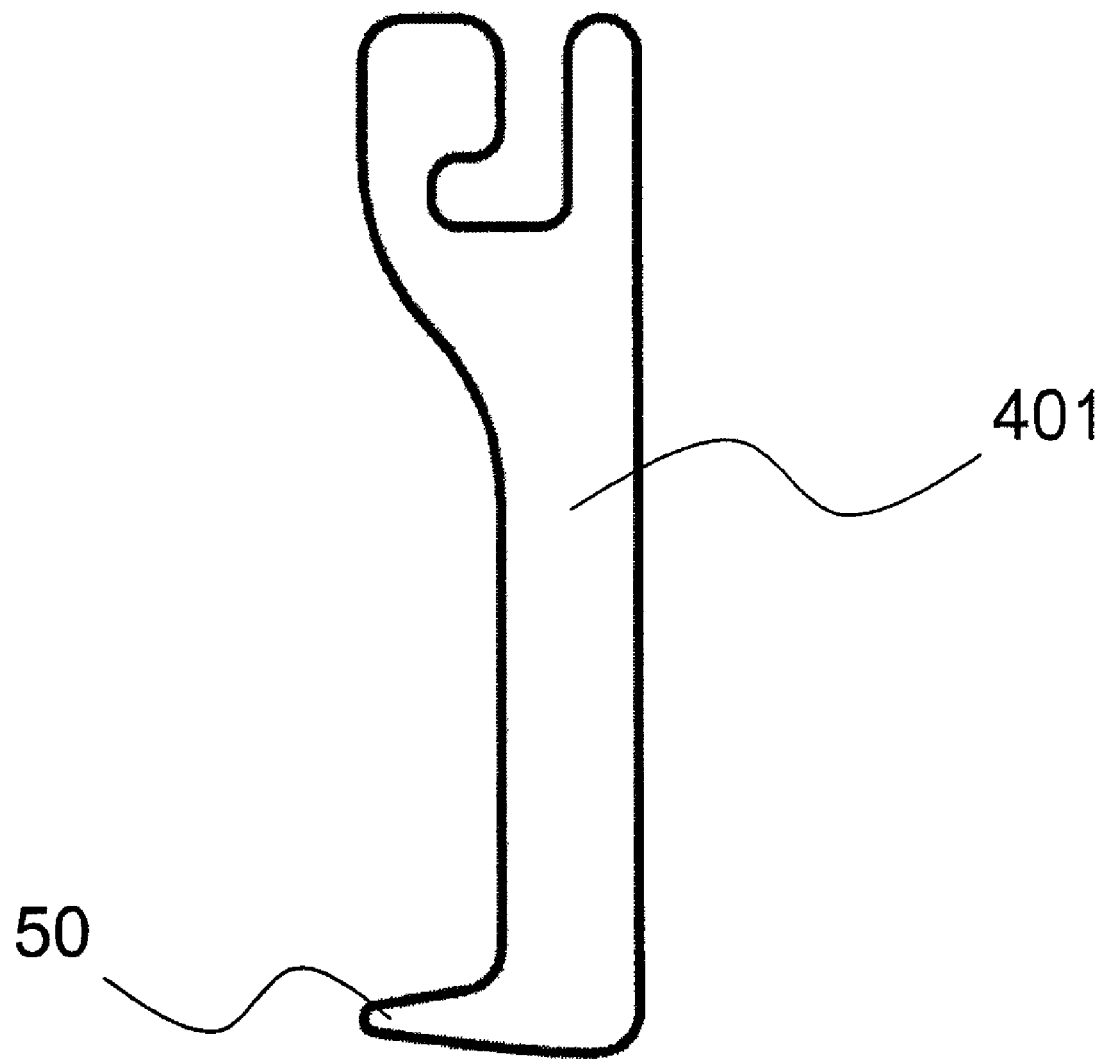
FIG. 5 is a profile view showing an embodiment of a sealing ring.

FIG. 5 shows a sealing ring 401 with a sealing lip 50 located at the bottom in a profile view.

Figure 6:
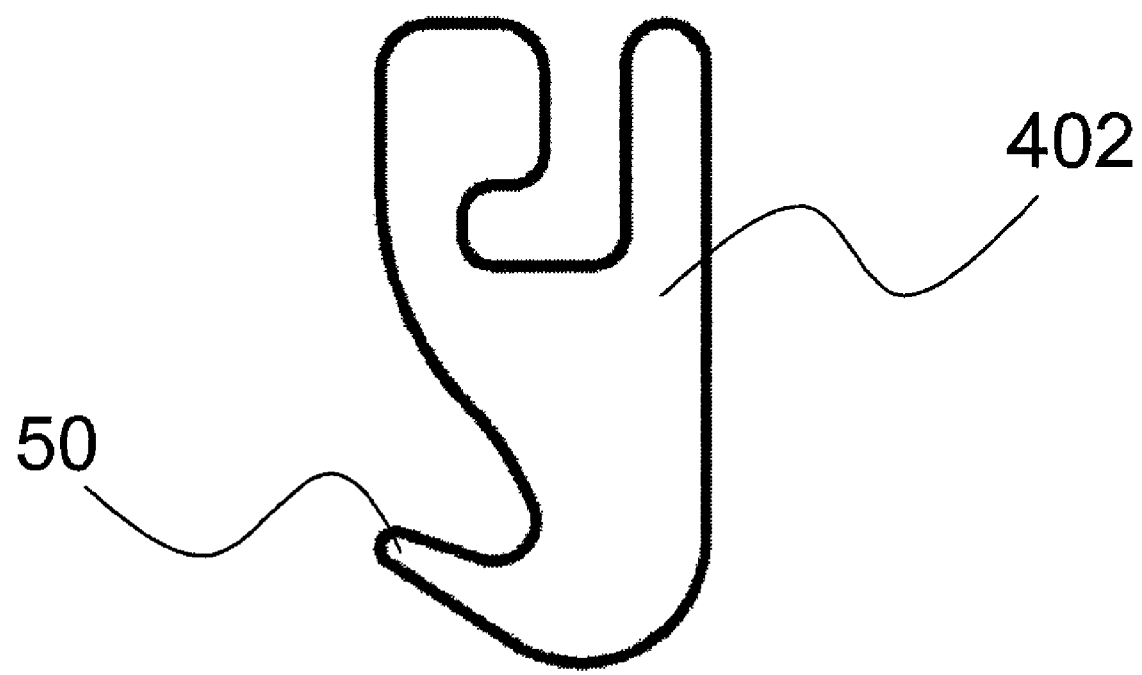
FIG. 6 is a profile view showing another embodiment of an sealing ring.

FIG. 6 shows, alternatively, a sealing ring 402 with the sealing lip 50 located on top in a profile view.

Figure 7:
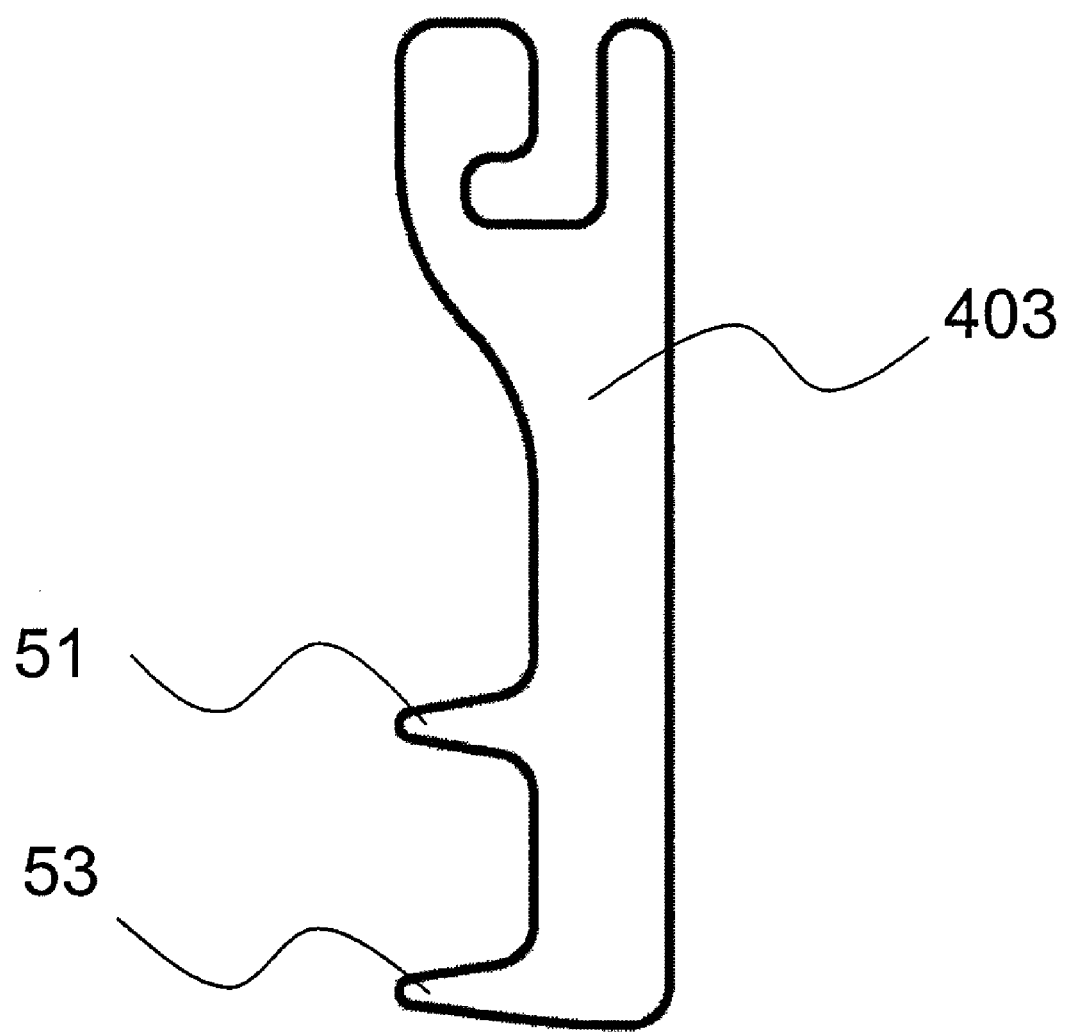
FIG. 7 is a profile view showing another embodiment of a sealing ring.

FIG. 7 shows, in another variant, a sealing ring 403 with a ring-shaped sealing lip 51 located on top and with a ring-shaped sealing lip 53 located at the bottom in a profile view.

Figure 8:
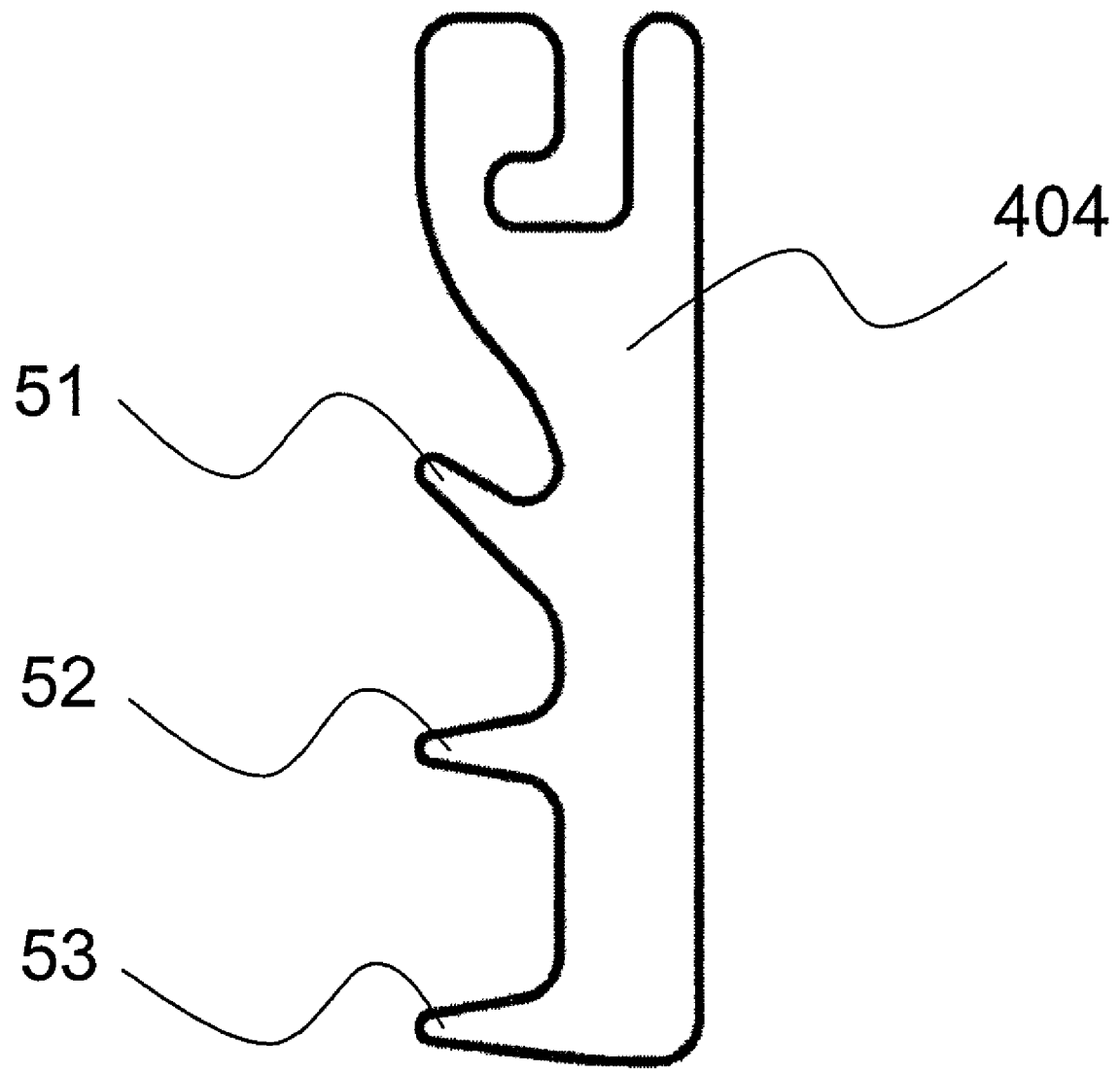
FIG. 8 is a profile view showing another embodiment of a sealing ring.

FIG. 8 shows, in an additional variant, a sealing ring 404 with a sealing lip 51 located at the top, with a sealing lip 52 located in the middle and with a sealing lip 53 located at the bottom in a profile view. Sealing lips 51, 52, 53 are all in contact with the jacket surface 34 of the outer valve crater 15.

Figure 9:
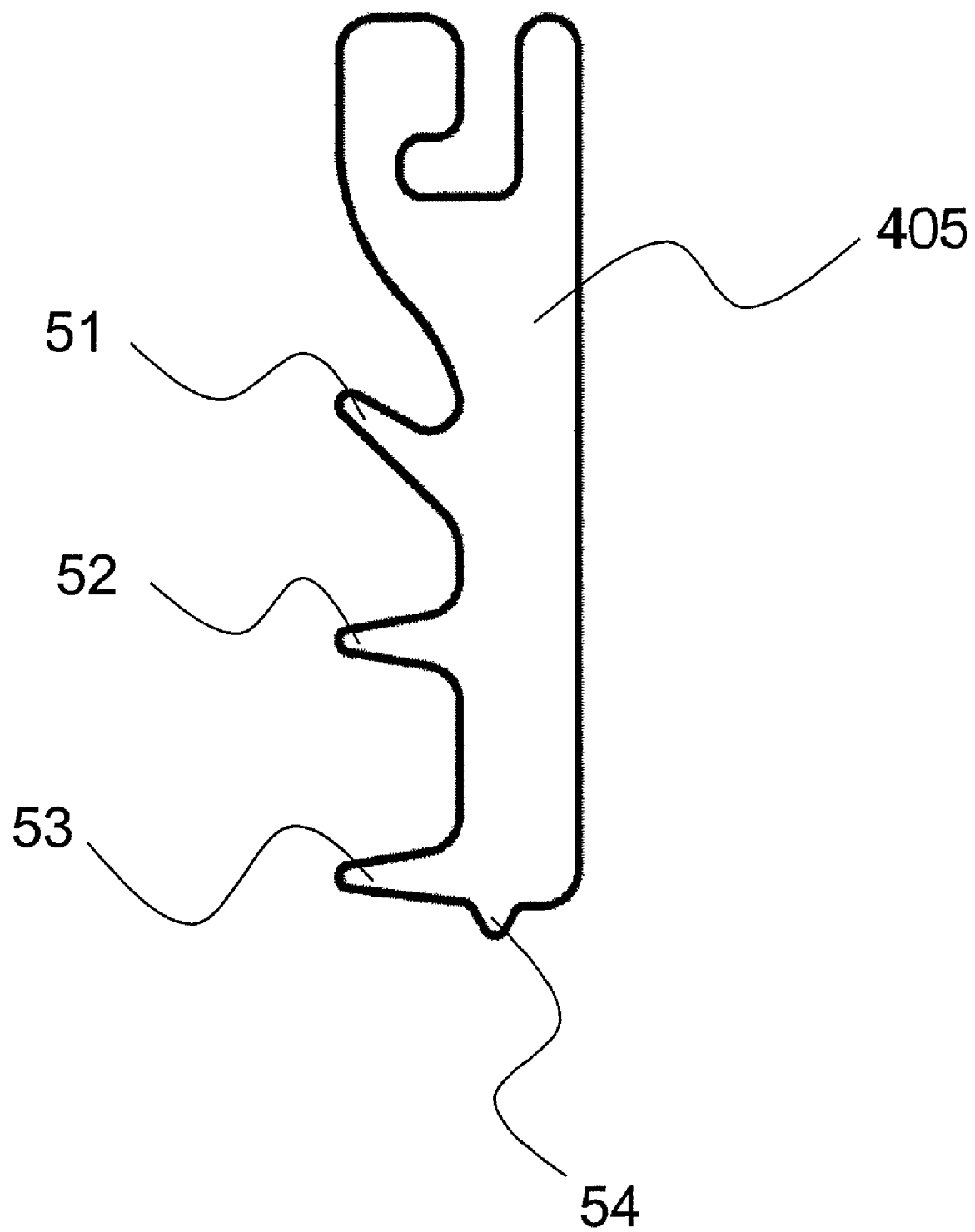
FIG. 9 is a profile view showing another embodiment of a sealing ring.

FIG. 9 shows, in another variant, a sealing ring 405 with a sealing lip 51 located at the top, with a sealing lip 52 located in the middle, with a sealing lip 53 located at bottom, and with a lower sealing lip 54, which are each of a ring-shaped design, in a sectional view.

Figure 10:
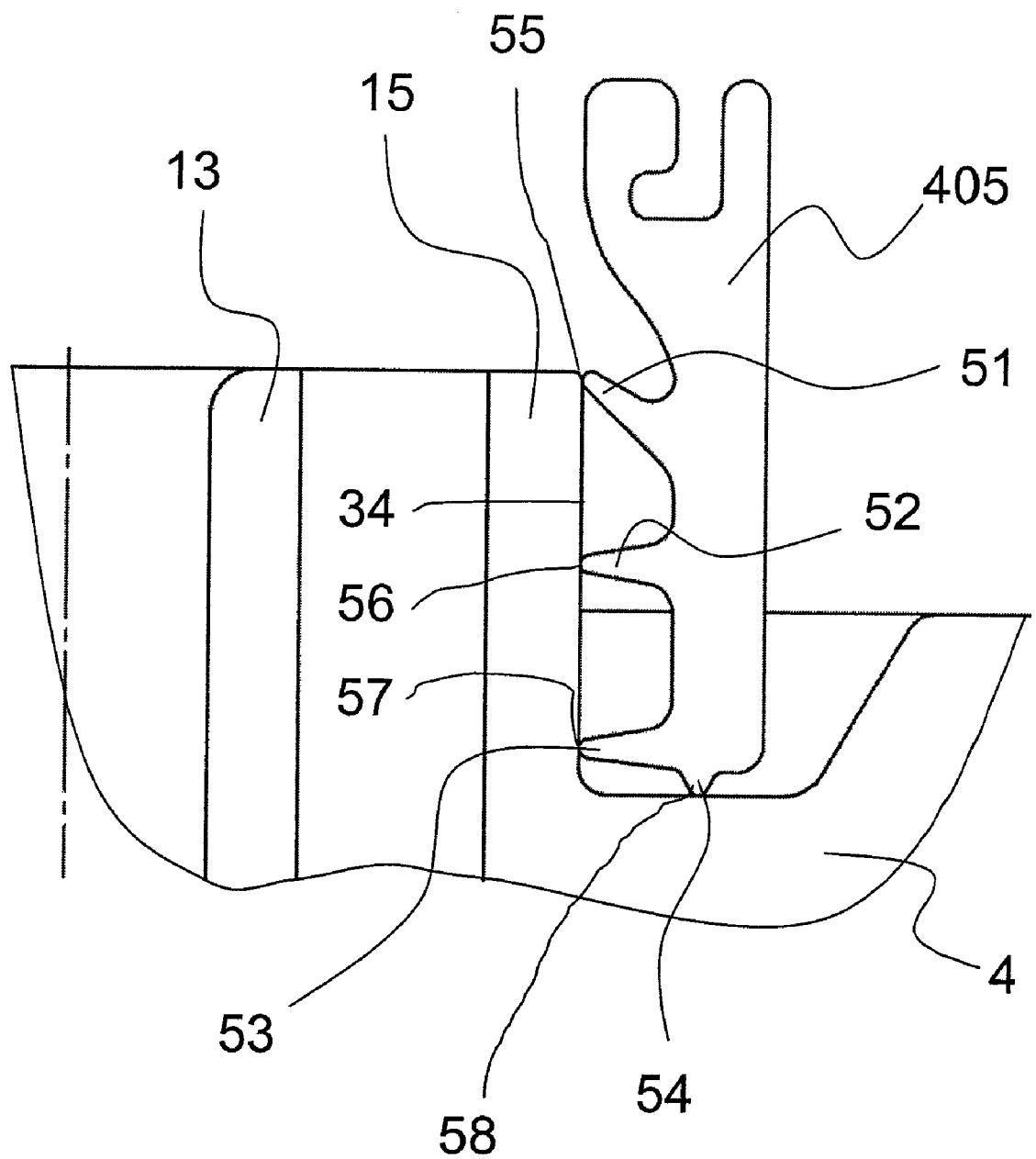
FIG. 10 is a schematic partial view of a cross section of the absorber container with a sealing ring in a profile view.

FIG. 10 shows the sealing ring 405 according to FIG. 9 in cooperation with the outer valve crater 15 of absorber container 4. The sealing lips 51, 52, 53 are in contact here with partial surfaces 55, 56, 57 of the jacket surface 34 of the outer valve crater 15. The lower sealing lip 54 is located at another partial surface 58 within the recessed surface 35.

While specific embodiments of the invention have been shown and described in detail to illustrate the application of the principles of the invention, it will be understood that the invention may be embodied otherwise without departing from such principles.

What is claimed is:

1. An adapter for adapting an absorber container to a breathing system, the absorber container comprising a first gas channel, with a jacket surface, and a second gas channel, with a jacket surface, said first gas channel and said second gas channel extending into a connection area between said absorber container and the adapter, the adapter comprising:
   an adapter housing cooperating with the absorber container to define the connection area;
   seals in the connection area and at said first gas channel and at said second gas channel and extending between said absorber container and said adapter, at least one of said seals comprising plural sealing surfaces extending to said jacket surface of one of said first gas channel and said second gas channel.

2. An adapter in accordance with claim 1, wherein said first gas channel comprises an inner gas channel and said second gas channel comprises an outer gas channel arranged concentrically to said inner gas channel.

3. An adapter in accordance with claim 2, wherein said second gas channel has an outer valve crater with an outer jacket surface provided as a sealing surface.

4. An adapter in accordance with claim 1, wherein in an area of said one of the first and second gas channel jacket surface said at least one of said seals has at least one sealing lip defining one of said sealing surfaces and extending in a ring-shaped pattern around said jacket surface of one of said first and said second gas channel.

5. An adapter in accordance with claim 4, wherein a plurality of said sealing lips are arranged at spaced locations from one another in an area of said jacket surface of one of said first and second gas channels and are in contact with partial surfaces of said jacket surface of one of said first and said second gas channels.

6. An adapter in accordance with claim 3, wherein a recessed surface is located below and adjacent to said valve crater of said outer gas channel as another sealing surface.

7. An adapter in accordance with claim 6, wherein said at least one of said seals has another sealing lip in the area of said recessed surface.

8. An absorber container arrangement for adaptation to a breathing system, the arrangement comprising:
   an absorber comprising a first gas channel with a jacket surface and a second gas channel with a jacket surface;

APPENDIX

LIST OF REFERENCE NUMBERS

| | | | |
|---|---|---|---|
| 1 | Adapter | 34 | Jacket surface |
| 2 | Valve means | 35 | Recessed surface |
| 3 | Mount | 36 | Top side |
| 4 | Absorber container | 401, 402, 403, 404, 405 | Sealing ring |
| 5 | Housing | 50 | Sealing lip |
| 6 | Connecting branch | 51 | Sealing lip located at top |
| 7 | Guide sleeve | 52 | Sealing lip located in the middle |
| 12 | Inner gas channel | 53 | Sealing lip located at bottom |
| 13 | Inner valve crater | 54 | Sealing lip on recessed surface |
| 14 | Outer gas channel | 55, 56, 57 | Partial surfaces of the jacket surface |
| 15 | Outer valve crater | 58 | Partial surface |
| 16 | First sealing ring | | |
| 17 | Outer sealing lip | | |
| 18 | Inner sealing lip | | |
| 21 | Wall section | | |
| 22 | Second sealing ring | | |
| 25 | Valve body | | |
| 26 | Sealing lip | | |
| 27 | Compression spring | | |
| 33 | Front surface | | | an absorber container to breathing system adapter comprising an adapter housing cooperating with the absorber container to define a connection area, each of said first gas channel and said second gas channel extending into said connection area between said absorber container and said adapter, and a plurality of seals, said seals sealing the connection area in a region of said first gas channel and at said second gas channel and extending between said absorber container and said adapter, at least one of said seals comprising plural sealing surfaces extending to said jacket surface of one of said first gas channel and said second gas channel.

9. An absorber container arrangement in accordance with claim 8, wherein said first gas channel comprises an inner gas channel and said second gas channel comprises an outer gas channel arranged concentrically to said inner gas channel.

10. An absorber container arrangement in accordance with claim 9, wherein said second gas channel has an outer valve crater with an outer jacket surface provided as a sealing surface.

11. An absorber container arrangement in accordance with claim 10, wherein in an area of said outer jacket surface said at least one of said seals has at least one sealing lip defining one of said sealing surfaces and extending in a ring-shaped pattern around said outer jacket surface.

12. An absorber container arrangement in accordance with claim 11, wherein a plurality of said sealing lips are arranged at spaced locations from one another in an area of said outer jacket surface and are in contact with partial surfaces of said outer jacket surface.

13. An absorber container arrangement in accordance with claim 12, wherein a recessed surface is located below and adjacent to said valve crater of said outer gas channel as another sealing surface and one of said plurality of said sealing lips is in contact with said recessed surface as another sealing surface.

* * * * *